(12) United States Patent
Wada et al.

(10) Patent No.: US 8,115,643 B2
(45) Date of Patent: Feb. 14, 2012

(54) EXCREMENT DETECTION SENSOR

(75) Inventors: Ichiro Wada, Kagawa (JP); Miou Suzuki, Kagawa (JP); Kiyoshi Toda, Tokyo (JP); Yuichi Hirai, Tokyo (JP); Masaho Hayashi, Tokyo (JP); Hiroshi Uematsu, Tokyo (JP); Toshihiko Uenishi, Fukuoka (JP)

(73) Assignee: Uni-Charm Corporation, Ehime (JP)

( * ) Notice: Subject to any disclaimer, the term of this patent is extended or adjusted under 35 U.S.C. 154(b) by 425 days.

(21) Appl. No.: 12/308,912

(22) PCT Filed: Jul. 18, 2006

(86) PCT No.: PCT/JP2006/314152
§ 371 (c)(1),
(2), (4) Date: Dec. 29, 2008

(87) PCT Pub. No.: WO2008/001475
PCT Pub. Date: Jan. 3, 2008

(65) Prior Publication Data
US 2009/0326493 A1 Dec. 31, 2009

(30) Foreign Application Priority Data
Jun. 29, 2006 (JP) .................................. 2006-180320

(51) Int. Cl.
*G08B 23/00* (2006.01)
*G08B 21/00* (2006.01)
*H01H 29/00* (2006.01)
*A61B 19/00* (2006.01)
*A61F 13/15* (2006.01)

(52) U.S. Cl. .................. 340/573.5; 340/604; 200/61.04; 200/61.05; 128/912; 604/361

(58) Field of Classification Search ............... 340/537.5, 340/604, 605, 620; 200/61.04, 61.05, 182, 200/235, 236; 600/300, 301; 128/917, 912; 324/694; 604/361, 327; 73/304 R, 170.17–170.21
See application file for complete search history.

(56) References Cited

U.S. PATENT DOCUMENTS

| 4,752,293 | A  | * | 6/1988 | Smith ........................ 604/322 |
| 6,246,330 | B1 | * | 6/2001 | Nielsen ...................... 340/604 |
| 6,395,955 | B1 | * | 5/2002 | Roe et al. ................... 604/361 |
| 7,394,391 | B2 | * | 7/2008 | Long .......................... 340/573.5 |
| 2004/0113801 | A1 | * | 6/2004 | Gustafson et al. ........... 340/604 |
| 2005/0023152 | A1 | * | 2/2005 | Surridge et al. ............. 205/775 |
| 2005/0195085 | A1 | * | 9/2005 | Cretu-Petra ................ 340/573.5 |

FOREIGN PATENT DOCUMENTS

JP       63-290950      11/1988
(Continued)

*Primary Examiner* — Benjamin C Lee
*Assistant Examiner* — Omeed Alizada
(74) *Attorney, Agent, or Firm* — Brinks Hofer Gilson & Lione (57) ABSTRACT

An excrement detection sensor in which two pairs of conductors 1, 2 and 3, 4 are formed between a carrier body 6 and a coating body 7 both having water-proof property and insulating property, wherein the cover body is formed with an urine introduction port 8 correlating the paired conductors and with a faeces introduction port 9 correlating the other paired conductors, and when urine enters into the urine introduction ports, the one pair of the conductors are short-circuited and when faeces enters into the faeces introduction ports, the other one pair of the conductors are short-circuited, whereby the urination and the evacuation can be distinctively detected.

14 Claims, 8 Drawing Sheets

FOREIGN PATENT DOCUMENTS

| | | |
|---|---|---|
| JP | 64-025049 | 1/1989 |
| JP | 10-030998 | 2/1998 |
| JP | 11-295250 | 10/1999 |
| JP | 11295250 A * | 10/1999 |
| JP | 2000-019136 | 1/2000 |
| JP | 2000-093448 | 4/2000 |
| JP | 2002-022688 | 1/2002 |
| JP | 2002-82080 | 2/2002 |
| JP | 2004-177120 | 8/2004 |
| JP | 2004-267517 | 9/2004 |

* cited by examiner

EXCREMENT DETECTION SENSOR

RELATED APPLICATIONS

The present application is a 35 U.S.C. §371 national stage filing of International Patent Application No. PCT/JP2006/314152, filed Jul. 18, 2006, to which priority is claimed under 35 U.S.C. §120 and through which priority is claimed under 35 U.S.C. §119 to Japanese Priority Patent Application No. 2006-180320, filed Jun. 29, 2006.

TECHNICAL FIELD

The present invention relates to an excrement detection sensor for detecting urination and faeces.

BACKGROUND ART

Generally, there is known a water content detection sensor for detecting presence or generation of water content at a time when the water content or water adheres between electrodes, and then, electric current passes (for example, refer to Patent Literature 1, 2, 3). Such water content detection sensors are utilized for an excrement receiver, a diaper and so on, and when the water content adheres between the electrodes by the urination, for example, the electrodes are short-circuited and the urination is thereby detected.

Moreover, there is also known an urine-gathering system in which the urine is received by an excrement receiver or a saucer inserted in a diaper, and the urine received in the saucer is sucked by a vacuum pump every time when the urination is detected(for example, refer to Patent Literature 4).
Patent Literature 1: JP-63-290950
Patent Literature 2: JP-2000-19136
Patent Literature 3: JP-2002-82080
Patent Literature 4: JP-2004-267517

DISCLOSURE OF THE INVENTION

Problems to be Solved by the Invention

As the conventional water content detection sensor is provided with only a pair of electrodes, it is difficult to discriminate whether either one of evacuation or urination is detected. In the use of such conventional water content detection sensor for the excrement receiver or diaper of the type of recovering the urine by the saucer, the vacuum pump is operated at the time of detecting the evacuation, and in such a case, there may cause clogging of a tube or vacuum pump with a solid component of the evacuation, which may result in difficulty of recovering the urine.

In addition, in the conventional water content detection sensor, an electrical potential is caused between electrodes, and when an electric current passes between the electrodes by the adhesion of the water content therebetween, a signal announcing the generation of the urination is merely outputted, so that it is difficult to discriminate quality or condition of the electrodes themselves. Because of this reason, there may cause a case such that no signal is generated due to defect of the electrodes in spite of the adhesion of the water content between the electrodes, and hence, the generation of the urination or presence of the urine cannot be detected, thus being inconvenient.

Furthermore, when the conventional water content detection sensor is utilized for the detection of the urination in the diaper, if the urination is detected at plural times, resistances may be changed as time elapses, which may result in erroneous operation of the detection sensor.

Accordingly, an object of the present invention is to substantially eliminate defects or drawbacks encountered in the prior art mentioned above and is to provide an excrement detection sensor capable of exactly detecting the generation of the excrement.

Means for Solving the Problems

The above and other objects can be achieved according to the present invention by providing an excrement detection sensor comprising:
two pairs of conductors (1,2,3,4) extending in parallel with each other;
a carrier body (6) on which the conductors are formed; and
a coating body (7) covering the conductors with the conductors being disposed between the carrier body (6) and the coating body,
wherein either one of the carrier body and the coating body (7) is formed with urine introduction ports (8) correlating at least one pair of conductors (1,2) and faeces introduction ports (9) correlating another one pair of conductors (3,4), in which when urine enters into the urine introduction ports (8), the one pair of the conductors (1,2) are short-circuited and when faeces enters into the faeces introduction ports (9), the another one pair of the conductors (3,4) are short-circuited.

In preferred embodiments, the following subject features may be attained.

That is, either one or another pair of conductors (1,2) may be connected through a high resistance conductor (14) having a resistance larger than that of the paired conductors (1,2).

An urine passing hole (15) may be formed so as to penetrate the carrier body (6) and the coating body (7).

The conductors (1,2,3,4,14) may be printed on the carrier body (6), and the coating body (7) is printed so as to cover the printed conductors.

The conductors (1,2,3,4,14) may be printed with conductive ink including conductive carbon. The conductors (1,2,3,4) are printed with conductive ink including conductive carbon of an amount larger than that included in the conductive ink of the high resistance conductor (14).

The carrier body (6) or coating body (7) formed with the urine introduction ports (8) may be formed as a lamination body composed of printing ink layers including at least one layer (7b) formed of urine resist ink. The lamination body may include at least one layer (7a) of solvent resist ink disposed between the urine resist ink layer (7b) and the conductors (1,2,3,4,14). The urine resist ink may be an urethane combined ink of polyester polyal and isocyanate or a UV hardened resin ink. The solvent resist ink may be polyester resin ink.

The conductors (1,2,3,4,14) may be printed with conductive ink including only of conductive carbon as conductive material.

EFFECTS OF THE INVENTION

According to the excrement detection sensor of the present invention of the characters mentioned above, The two pairs of conductors (1,2,3,4) are formed between a carrier body (6) and a coating body (7) both having water-proof property and insulating property, wherein the coating body (7) or carrier body (6) is formed with an urine introduction port (8) correlating the paired conductors (1,2) and with a faeces introduction port (9) correlating the other paired conductors (3,4), and when urine enters into the urine introduction ports (8), the one pair of the conductors (1,2) are short-circuited and when faeces enters into the faeces introduction ports (9), the other one pair of the conductors (3,4) are short-circuited, whereby the urination and the evacuation can be distinctively detected. Therefore, even in a case where the excrement detection sensor is applied to an excrement receiver (17) for recovering the urine by using a saucer (16) or to a diaper, the clogging, due to the faeces, of the tube (18) of a suction machine such as vacuum pump for recovering the urine can be effectively prevented, and hence, the urine can be recovered in plural times.

Furthermore, according to the present invention, when the paired conductors (1,2) are connected through a high resistance conductor (14) having a resistance higher than that of the paired conductors, an electric current passes between the conductors (1,2) through the high resistance conductor (14), so that the quality of the conductors (1,2) can be confirmed and the urination and evacuation can be thereby exactly detected.

In addition, according to the present invention, the coating body (7) or carrier body (6) to which the urine introduction ports (8) and the faeces introduction ports (9) are formed is formed as a lamination body of printed ink layers, and at least one (7b) of the layers is formed of an urine resist ink. In such case, if a plurality of urinations are detected, the resistances of the conductors (1,2,3,4,14) do not change. Therefore, the generation of the urination can be exactly detected at a plurality of times.

EXPLANATION OF REFERENCE NUMERAL

1,2,3,4 . . . conductor, 5 . . . excrement detection sensor, 6 . . . carrier body, 7 . . . coating body, 7a . . . solvent resist ink layer, 7b . . . urine resist ink layer, 8 . . . urine introduction port, 9 . . . faeces introduction port, 14 . . . high resistance conductor, 15 . . . urine passing hole

BEST MODE FOR CARRYING OUT THE INVENTION

Hereunder, a best mode for embodying the invention will be explained with reference to the accompanying drawings.

First Embodiment

With reference to FIGS. 1 to 5, in an excrement detection sensor 5 of this embodiment, two pairs of conductors 1, 2 and 3, 4 extending in parallel are sandwiched between a carrier body 6 and a coating body 7, both having water-proof property and insulating property. The coating body 7 is formed with an urine introduction port 8 correlating at least one pair of conductors 1 and 2, and a faeces introduction port 9 correlating the other pair of conductors 3 and 4, and when the urine A enters into the urine introduction port 8, the one pair of conductors 1 and 2 is short-circuited, and on the other hand, when the faeces B enters into the faeces introduction port 9, the other pair of conductors 3 and 4 are short-circuited.

Figure 1:
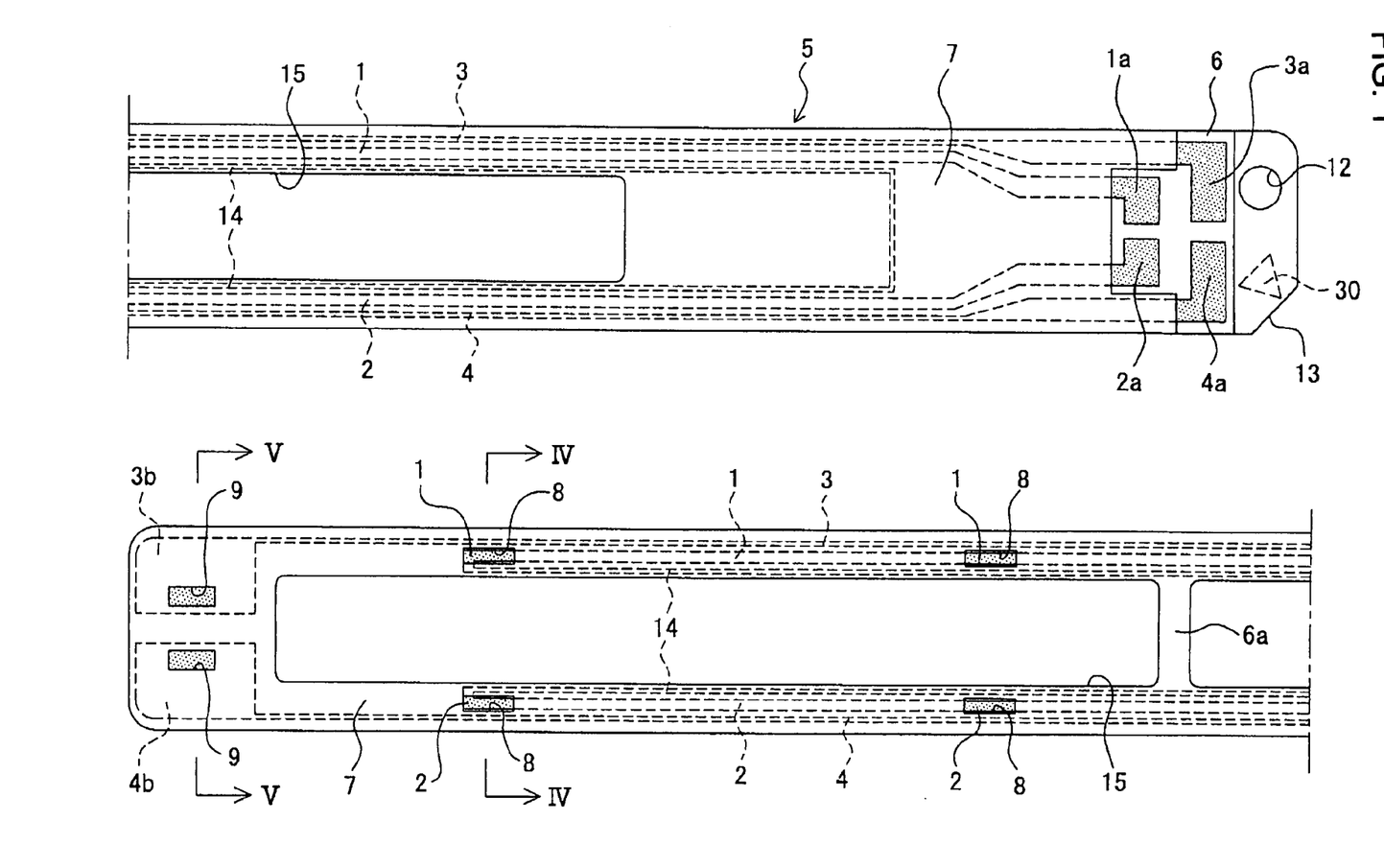
FIG. 1 is an illustrated front view of an excrement detection sensor according to a first embodiment of the present invention.
Figure 2:
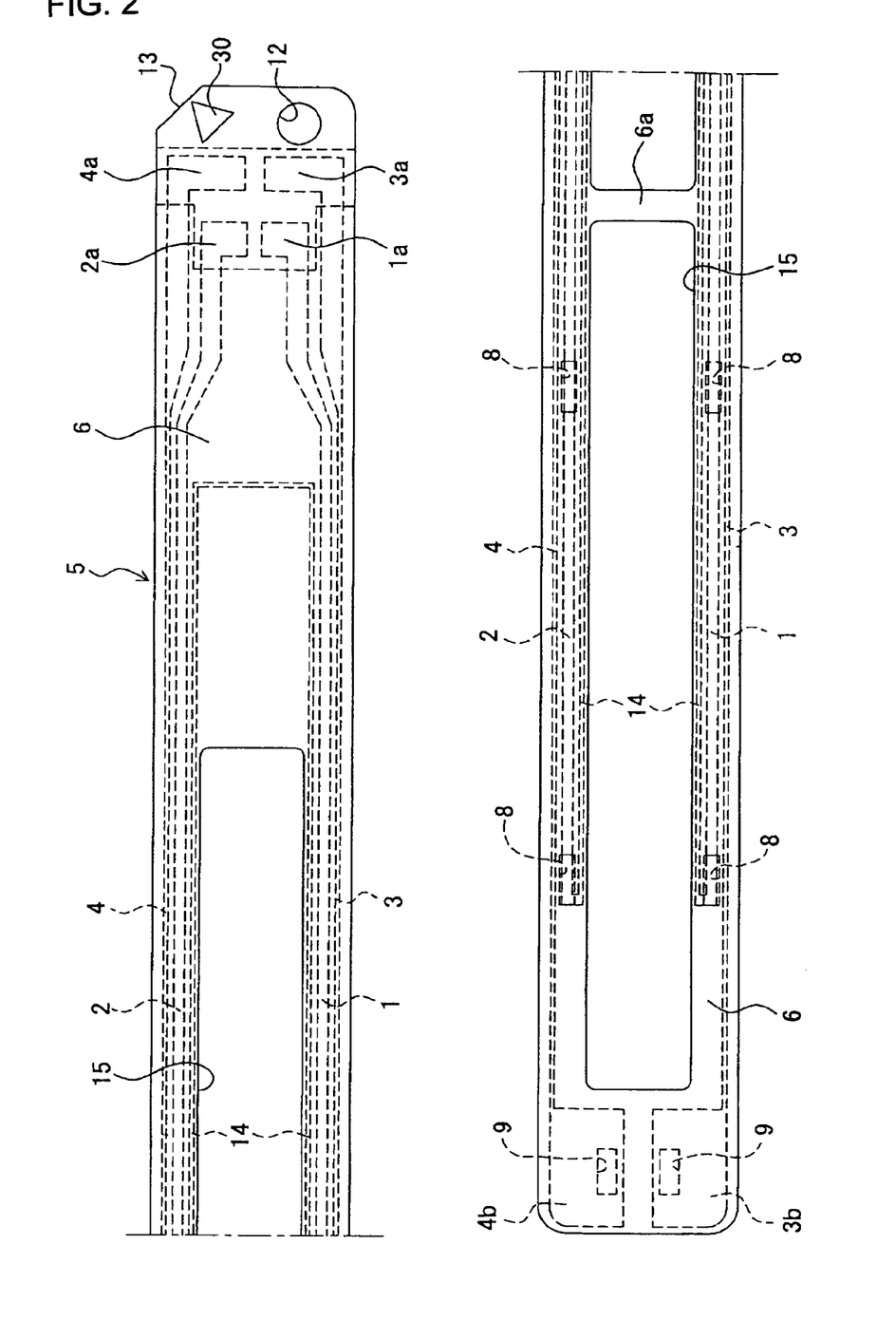
FIG. 2 is an illustrated rear view of the excrement detection sensor of FIG. 1.

The carrier body 6 carries the entire structure of the excrement detection sensor 5 of this embodiment and has a belt-like shape which is bendable or flexible. The carrier body 6 has, for example, a length slightly longer than a length of crotch height of a human body. The carrier body 6 has a water-proof property and electrically insulating property. In order to confirm the quality of the circuit portion such as conductors 1, 2, 3 and 4, it is desired that the carrier body 6 is transparent. The carrier body 6 is formed from a biaxial orientated film of polypropylene, polyethylene, polyvinyl chloride, polyester, polyamide, polyimide, polyamideimide, polycarbonate, polystyrene, or the like. The carrier body 6 has a thickness of, preferably, 30 μm to 300 μm, and more preferably, 50 μm to 100 μm. It may be possible for the carrier body to be formed of an opaque material, but it may be desired to be formed from a transparent or translucent material.

Figure 10:
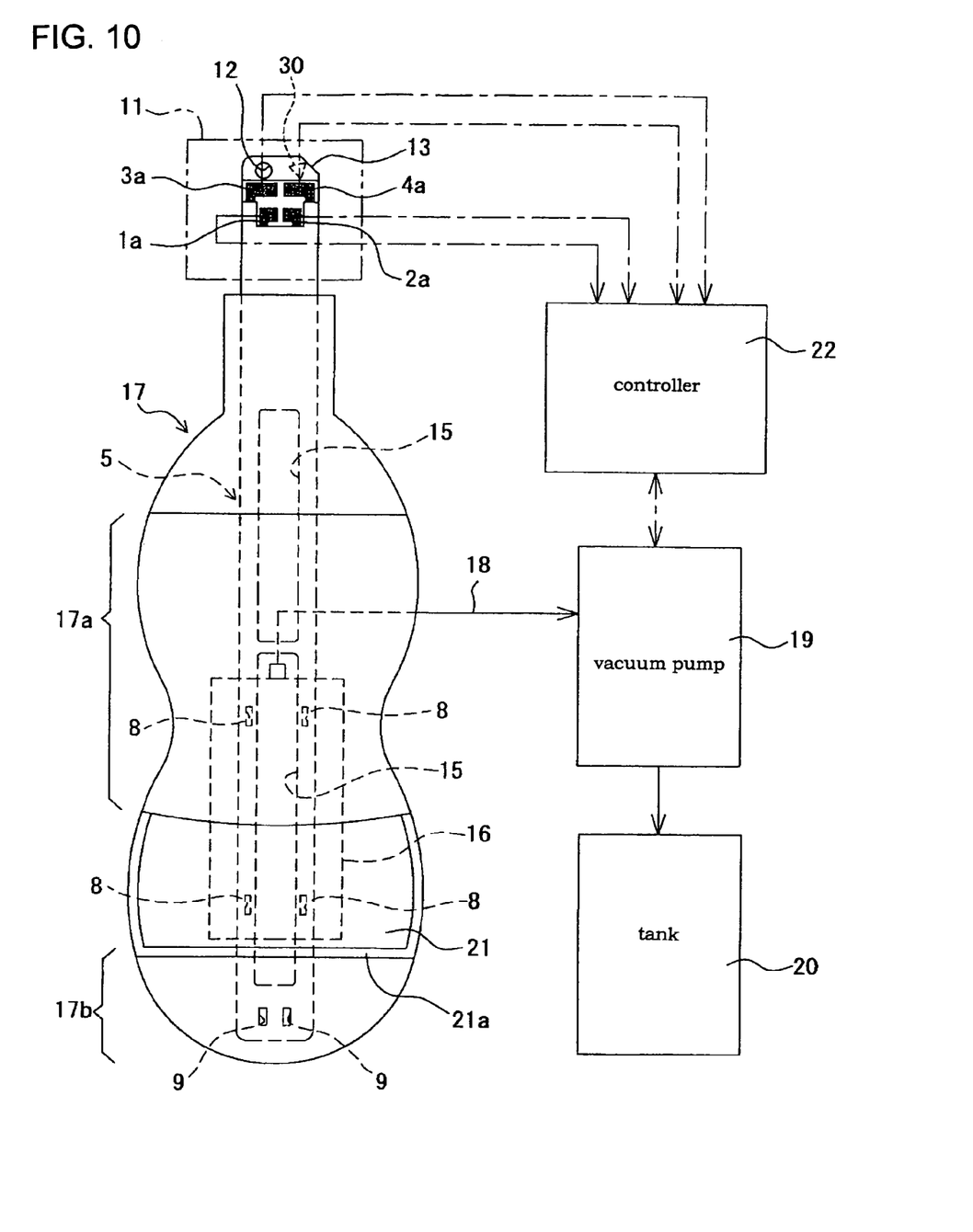
FIG. 10 is a conceptual view showing a used example of the excrement detection sensor according to the present invention.

A positioning hole 12 for connecting the carrier body 6 to a connector 11 shown in FIG. 10 is formed, as occasion demands, to a base end of the carrier body 6. A cutout 13 and/or marker 30 may be provided, as occasion demands, for discriminating or showing positional relationship between the excrement detection sensor 5 and the connector 11.

Figure 3:
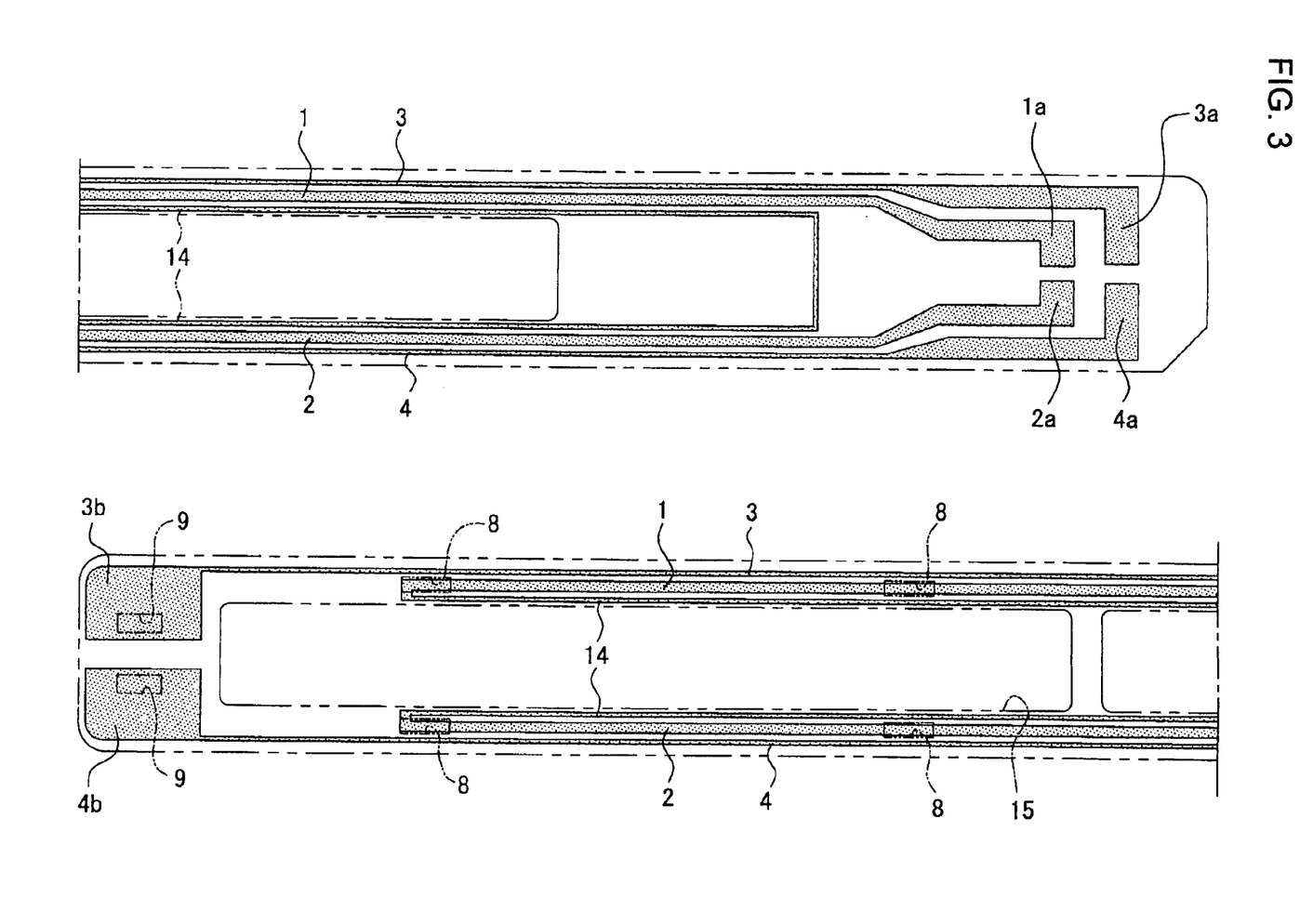
FIG. 3 is a plan view showing a circuit portion.

The two pairs of conductors 1, 2 and 3, 4 mentioned above have relatively low-resistance and extend along both side edges of the belt-shaped carrier body 6. In these conductors, an inside pair of conductors 1 and 2 are utilized for detecting urination and an outside pair of conductors 3 and 4 are utilized for detecting evacuation. Terminal portions 1a, 2a and 3a, 4a, each having a relatively large area, are formed to base ends of the two paired conductors 1, 2 and 3, 4 so as to be connected to the connector 11. Expanded portions 3b and 4b are also formed to tail ends opposing to the base ends connecting the connector 11 of the conductors 3 and 4 for detecting the evacuation. These expanded portion 3b and 4b are formed to the tail end of the carrier body 6, but the tail ends of the conductors 1 and 2 for detecting the urination are ended at portions near the base end side other than the expanded portions 3b and 4b. of the conductors 3 and 4 for detecting the evacuation. That is, the tail ends of the conductors 1 and 2 for detecting the urination and their neighbouring portions, and the expanded portions 3b and 4b of the conductors 3 and 4 for detecting the evacuation correspond, respectively, to urination portion and evacuation portion of a human body.

The conductors 1, 2, 3 and 4 inclusive of the terminal portions 1a, 2a, 3a and 4a and the expanded portions 3b and 4b are formed by printing conductive ink on the carrier body 6. The conductive ink is prepared by kneading a binder, conductive metal powder and a filler. As such binder, there is used polyvinyl chloride group resin, polyacrylic group resin, epoxy group resin, polyester group resin, polyacrylic urethane group resin, polyolefin group resin, polyurethane group resin, phenol group resin or the like. As such conductive metal powder, there is used silver, gold, copper, nickel, aluminium, conductive carbon or the like. As such filler, there is used a viscosity controlling agent, dispersant or the like. The conductive ink is coated, in fine belt shape, on the carrier body 6 through screen printing, direct gravure printing, flexographic printing or like printing to thereby form the conductors 1, 2, 3 and 4.

The conductors 1 and 2 for detecting the urination are printed with, for example, a width of 1.5 mm and a thickness of 10 μm, preferably, 5 to 30 μm. On the other hand, the conductors 3 and 4 for detecting the evacuation are printed with, for example, a width of 0.5 mm and a thickness of 10 μm, preferably, 5 to 30 μm. These conductors 1, 2, 3 and 4 have relatively low resistance, and the resistance is set preferably, for example, to 0 to 200 kΩ, and more preferably, less than 100 kΩ, by adjusting the content of the conductive metal powder in the conductive ink. In this first embodiment the resistance is about 100 kΩ.

The paired conductors 1 and 2 for detecting the urination are connected together through a high resistance conductor 14 having a resistance larger than that of the conductors 1 and 2. The resistance of the high resistance conductor 14 may be set preferably to 1 MΩ to 10 MΩ, and more preferably, to 2 MΩ to 6 MΩ.

This high resistance conductor 14 is disposed so as to extend along inside the respective conductors 1 and 2. That is, the high resistance conductor 14 first extends from the tail end of the conductor 1 toward the base end thereof, and on the way, extends toward the other conductor 2 and then extends toward the tail end thereof along the conductor 2. As a result, the high resistance conductor 14 and the paired conductors 1 and 2 constitute a single conductor on the carrier body 6, and when a potential difference is caused between the terminals 1*a* and 2*a* of the paired conductors 1 and 2, and electric current of a constant amount passes.

The high resistance conductor 14 is printed through a printing method as like as that mentioned with respect to the printing of the conductors 1 and 2 with a conductive ink having the component similar to that for the conductors 1 and 2. However, the high resistance conductor 14 has less amount of the conductive metal powder of the conductive ink, and as a result, the resistance of the high resistance conductor 14 is set to about several MΩ, for example, which is larger than that of the conductors 1 and 2. In addition, the high resistance conductor has a fine thickness, for example of about 0.5 mm, less than that of the conductors 1 and 2 for easy visual confirmation thereof.

Figure 4:
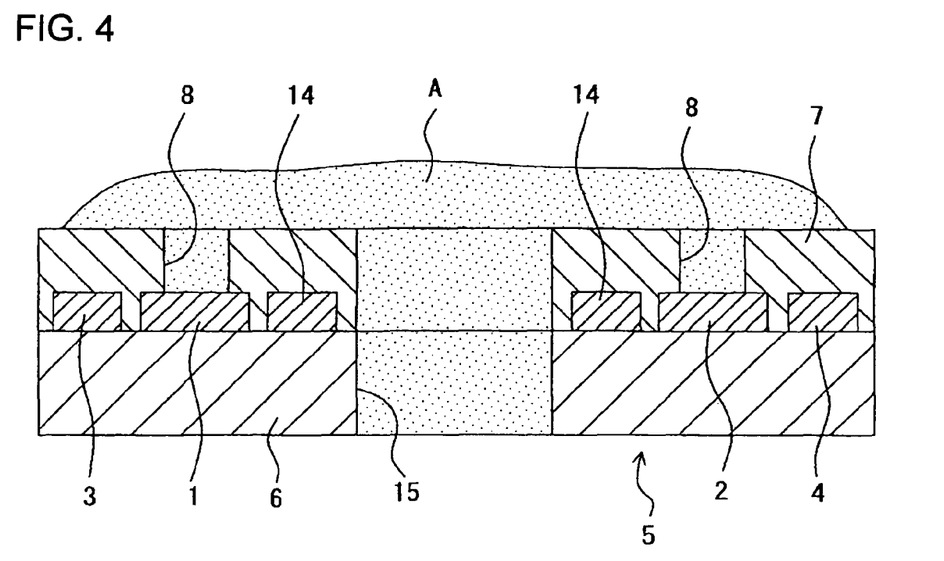
FIG. 4 is a sectional view taken along the line IV-IV in FIG. 1.
Figure 5:
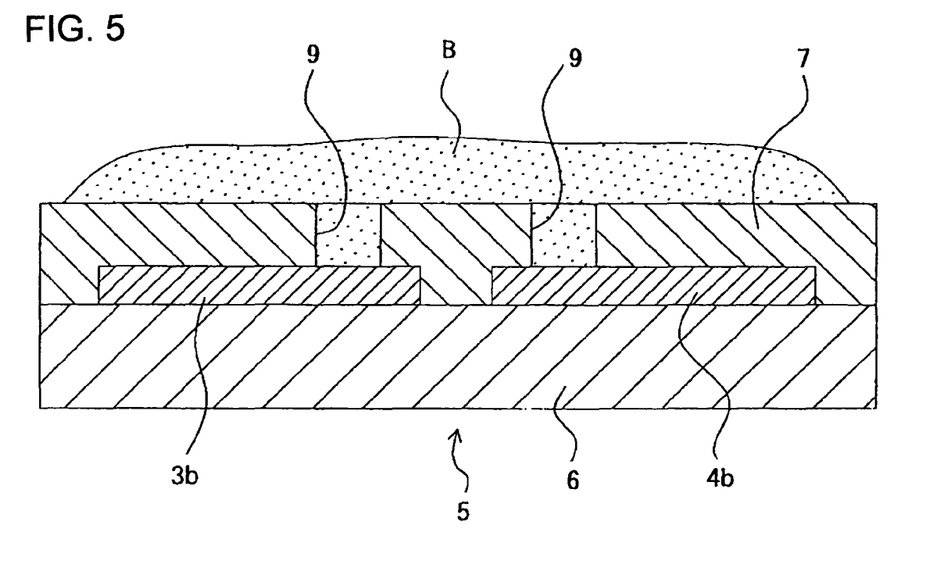
FIG. 5 is a sectional view taken along the line V-V in FIG. 1.

The coating body 7 is applied in layer on substantially the entire surface of the carrier body 6, above the conductors 1 and 2 and the high resistance conductor 14, except the portions of the terminals 1*a*, 2*a*, 3*a* and 4*a* and various introduction holes 8 and 9 mentioned hereinafter. The coating body 7 serves to electrically insulate the conductors 1, 2, 3 and 4, the high resistance conductor 14, and expanded portions 3*b* and 4*b* together with the carrier body 6 from the external portion.

Specifically, the coating body 7 is formed with a printing ink. The printing ink is prepared by kneading a binder, a pigment and a filler. As the binder, there is used polyvinyl chloride group resin, polyacrylic group resin, epoxy group resin, polyester group resin, polyacrylic urethane group resin, polyolefin group resin, polyurethane group resin, phenol group resin or the like. Further, as such binder, urethane-combined polyester polyal and isocyanate, or UV hardened resin may be utilized. As the pigment, there may be used, for example, a white pigment for clearly distinguishing it from the carrier body 6, the conductors 1, 2, 3 and 4, and the high resistance conductor 14. As the filler, there is used a viscosity controlling agent, dispersant or the like. This printing ink is coated on the carrier body 6 and the conductors 1, 2, 3 and 4 exclusive of predetermined portions such as terminal portions 1*a*, 2*a*, 3*a* and 4*a* through screen printing, direct gravure printing, or like printing to thereby form the coating body 7.

This coating body 7 attains function of insulating film and water-proof film.

The coating body 7 is formed with an urine introduction port 8 for introducing the urine by locally exposing the paired conductor 1 and 2 for the urination detection. The four urine introduction ports 8 are formed at the terminal portions, or near, of the conductors 1 and 2 for the urination detection such that respectively two ports are formed laterally symmetrically on both sides of the carrier body 6 with the longitudinal center line thereof being symmetry axis. Of course, less or more number of the urine introduction ports 8 may be adopted. The positions of the urine introduction ports 8 correspond to urination portion of a human body or near.

As shown in FIG. 4, when the urine A adheres to the conductors 1 and 2 so as to straddle the urine introduction port 8, the conductors 1 and 2 are short-circuited and then electric current passes. This current has a value larger than that in the case of no short-circuit, whereby the discharge of the urine A (i.e., urination) can be detected.

Furthermore, the coating body 7 is formed with a faeces introduction port 9 for introducing the faeces by locally exposing the paired conductors 3 and 4 for the faeces detection. The two faeces introduction ports 9 are formed at the expanded portions 3*b* and 4*b* of the conductors 3 and 4 for the faeces detection such that respectively one port 9 is formed laterally symmetrically on both sides of the carrier body 6 with the longitudinal center line thereof being symmetry axis. Of course, more number of the faeces introduction ports 9 may be adopted. The positions of the faeces introduction ports 9 correspond to evacuation portion of a human body or near.

As shown in FIG. 5, when the faeces B adheres to the conductors 3 and 4 so as to straddle the faeces introduction port 9, the conductors 3 and 4 are short-circuited and then electric current passes, whereby the discharge of the faeces B (i.e., evacuation) can be detected.

These urine introduction ports 8 and the faeces introduction ports 9 are formed by being printed as non-printed portions at the same time as the printing time of the coating body 7. By forming the coating body 7 by the printing operation, the urine introduction ports 8 and the faeces introduction ports 9 can be precisely formed at small sizes. In the illustrated embodiment, although these ports 8 and 9 have rectangular shapes, they may be formed so as to provide circular shapes, elliptical shapes, square shapes and the like as occasion demands.

The carrier body 6 is also formed with an urine passing hole 15 so as to penetrate the carrier body 6 in its thickness direction. In the illustrated embodiment, the urine passing hole 15 is punched to portions between parallelly extending of the high resistance conductor 14 of the carrier body 6. More specifically, two urine passing holes 15, each having a rectangular shape, are disposed in parallel, with a connection portion 6*a* remaining, in the longitudinal direction of the carrier body 6. The urine passing hole 15 may be composed of an aggregation of a number of small holes or formed with various shapes or modes. According to this structure, the urine discharged from the human body passes through the carrier body 6 from the front surface side to the rear surface side and then received by a receiving saucer 16, mentioned herein later. The urine passing hole 15 may be formed, for example, through a punching process after the printing of the conductors 1, 2, 3 and 4, and the coating body 7.

Hereunder, the operation of the excrement detection sensor of the above embodiment will be described.

Since the conductors 1, 2, 3 and 4, the high resistance conductor 14 and the coating body 7 of the excrement detection sensor 5 are formed on the transparent film by being printed with inks having different colors, the presence or absence of disconnection (break of wire) of the conductors 1, 2, 3 and 4 and the presence or absence of defect of the coating body 7 can be also visually confirmed, thus simplifying the selection of quality of the excrement detection sensor 5 as a product.

The excrement detection sensor 5 is used, as shown in FIG. 10, in a state of being sandwiched between various laminated sheets of non-woven fabric of a pad-shaped excrement receiver 17. In FIG. 10, reference numeral 17a denotes a portion receiving urine of the excrement receiver 17, and reference numeral 17b is a portion for receiving evacuation. The urine introduction port 8 of the excrement detection sensor 5 is positioned directly below the urine receiving portion 17a, and the faeces introduction port 9 of the excrement detection sensor 5 is positioned directly below the faeces receiving portion 17b.

Further, the urine receiving saucer 16 is disposed below the excrement detection sensor 5 at the urine receiving portion 17a in the excrement receiver 17. The saucer 16 is connected to a suction machine 19 such as vacuum pump through the tube 18, and the urine in the saucer 16 is delivered to the tank 20 by means of the suction machine 19.

Furthermore, a bag portion 21, for example, as sectioning means, for sectioning the urine receiving portion 17a and the faeces receiving portion 17b is formed to the excrement receiver 17. The bag portion 21 is formed by covering a sheet formed of non-woven fabric from the faeces receiving portion 17b to a rear half portion of the urine receiving portion 17a and heat-sealing it on a seal line 21a. By the presence of the bag portion 21, the urine can be prevented from entering into the faeces receiving portion 17b and the faeces can be prevented from moving to the urine receiving portion 17a.

The excrement receiver 17 is detachably mounted to a diaper, not shown, and is applied to a groin of a human body through the diaper.

The connector 11 electrically connected to a controller 22 is connected detachably to the base end portion of the excrement detection sensor 5. The connector 11 is accurately mated in position with the excrement detection sensor 5 by utilizing the positioning hole 12 and the cutout 13 formed to the base end portion of the excrement detection sensor 5, and on the other hand, the terminals 1a, 2a, 3a and 4a of the excrement detection sensor 5 are electrically connected to the terminals, not shown, on the connector side.

The controller 22 processes by using a CPU, not shown, a signal sent from the excrement detection sensor 5 and then generates various signals. The controller 22 applies a voltage between the terminals 1a and 2a of the paired conductors 1 and 2, and when a constant amount of current passes to the conductors 1 and 2 through the high resistance conductor 14, it is judged that the conductors 1 and 2 include no disconnection and are normal. On the contrary, when the constant amount of current does not pass between the conductors 1 and 2, it is judged that the conductors 1 and 2 are disconnected and an alarm is generated.

When a person wearing a diaper discharges urine, the urine infiltrates an urine receiving portion of the excrement receiver 17, and then, penetrates on the excrement detection sensor side. Thereafter, the urine invades into the urine introduction port 8 in contact to the surface of the excrement detection sensor 5 as shown in FIG. 4 to thereby short-circuit the paired conductors 1 and 2. According to this short-circuit, a signal indicating the generation of urination is generated from the excrement detection sensor 5 to the controller 22, which then operates the suction machine 19, and as occasion demands, an alarm, not shown, is operated. The urine passes through the urine passing hole 15 of the excrement detection sensor 5, is received by the saucer 16 and delivered to the tank 20 from the suction machine 19.

When a person wearing the diaper discharge faeces, the water content of the faeces infiltrate the faeces receiving portion 17b of the excrement receiver 17 and penetrates it on the excrement detection sensor side. Thereafter, the water content invades into the faeces introduction port 9 in contact to the surface of the excrement detection sensor 5 as shown in FIG. 5 to thereby short-circuit the other paired conductors 3 and 4. According to this short-circuit, a signal indicating the generation of evacuation is generated from the excrement detection sensor 5 to the controller 22, which then operates an alarm, not shown, to announce the generation of the evacuation.

Second Embodiment

Figure 6:
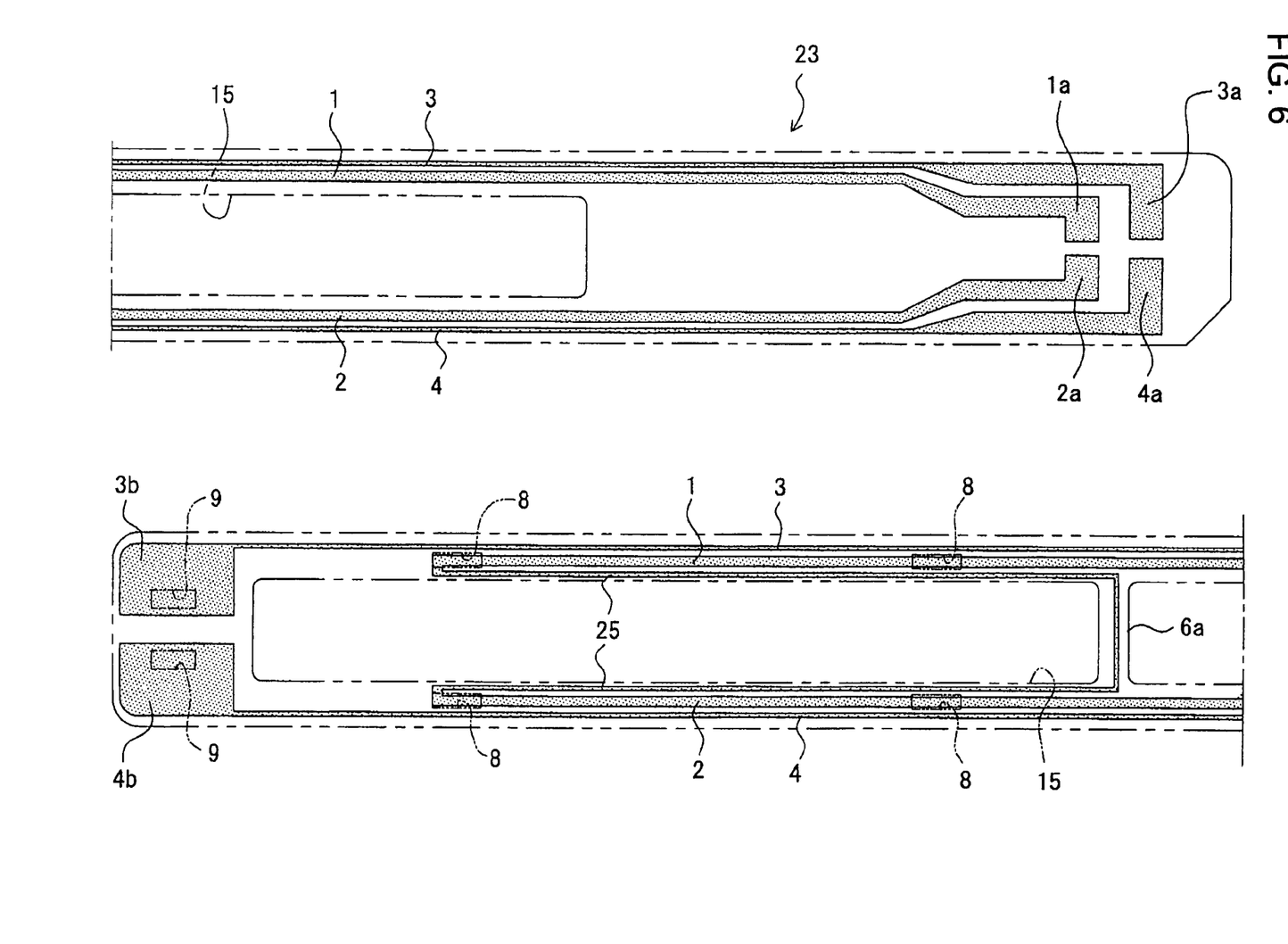
FIG. 6 is a plan view of a circuit portion of an excrement detection sensor according to a second embodiment of the present invention.

In this second embodiment, as shown in FIG. 6, a high resistance conductor 25 in the circuit portion of the excrement detection sensor 23 is made short in comparison with that of the first embodiment. That is, the high resistance conductor 25 is connected, at its one end, to the tail end of one of the conductors 1, extends along this conductor 1 to its base end side, passes, on the way of the extension, the connection portion 6a between the urine passing holes 15, 15 of the carrier body 6, extends toward the other conductor 2, and then is connected to the tail end of the conductor 2.

Further, in this second embodiment, the same reference numerals are added to members or elements corresponding to those in the first embodiment and duplicated explanation is omitted herein.

Third Embodiment

Figure 7:
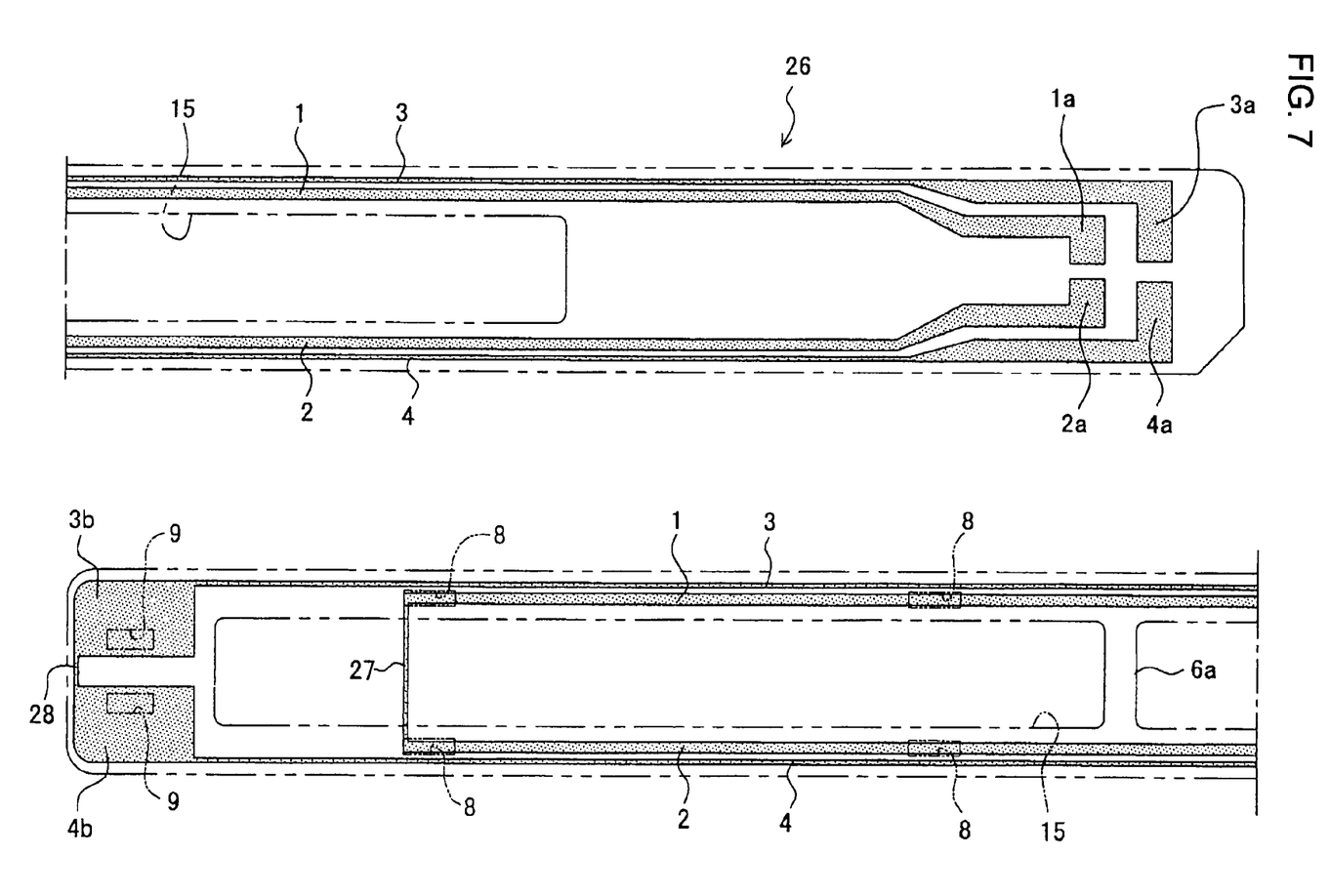
FIG. 7 is a plan view of a circuit portion of an excrement detection sensor according to a third embodiment of the present invention.

In this third embodiment, as shown in FIG. 7, a high resistance conductor 27 connecting the urine detection conductors 1 and 2 of an excrement detection sensor 26 is made further short in comparison with that of the second embodiment so as to extend linearly between two conductors 1 and 2 in the width direction of the carrier body 6.

In addition, another high resistance conductor 28 is arranged between the other paired faeces detection conductors 3 and 4. This high resistance conductor 28 connects linearly the expanded portions 3b and 4b of the conductors 3 and 4. According to this structure, a voltage is applied between the terminals 3a and 4a of the paired conductors 3 and 4 to thereby pass the electric current to the conductors 3 and 4 for the faeces detection. In this detection, when a current of a predetermined amount passes, it is judged that no disconnection is present on the conductors 3 and 4, and on the contrary, when the current of not predetermined amount passes, it is judged that the excrement detection sensor is considered to be defective, and is exchanged with a normal product.

Further, in this third second embodiment, the same reference numerals are added to members or elements corresponding to those in the first or second embodiment and duplicated explanation is omitted herein.

Fourth Embodiment

Figure 8:
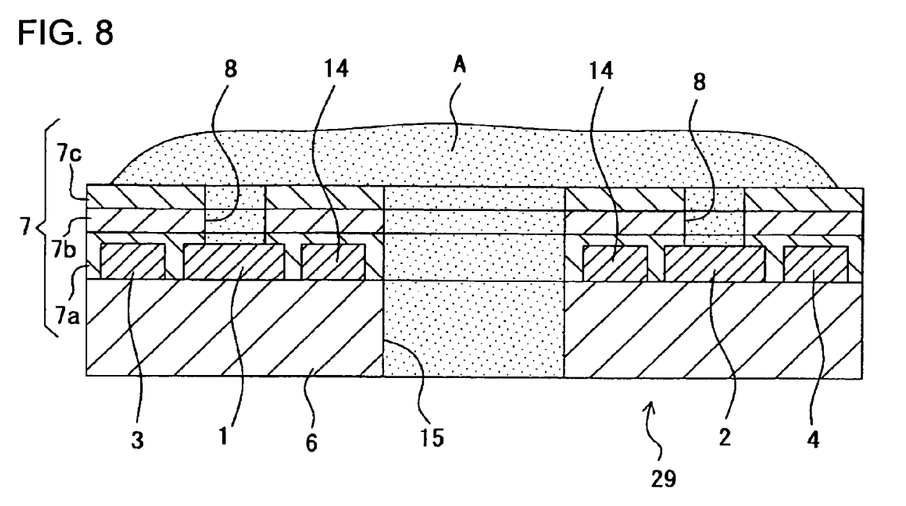
FIG. 8 is a sectional view, like FIG. 4, of an excrement detection sensor according to a fourth embodiment of the present invention.
Figure 9:
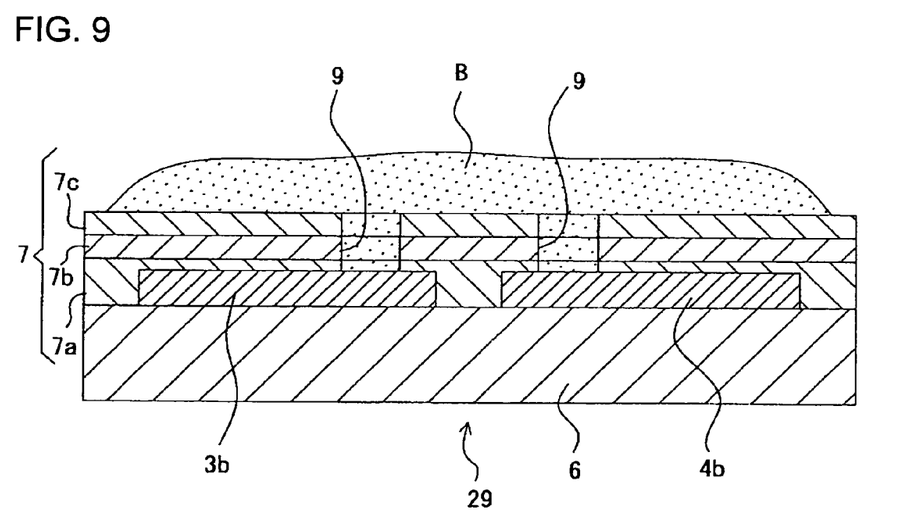
FIG. 9 is a sectional view, like FIG. 5, of an excrement detection sensor according to a fourth embodiment of the present invention.

In an excrement detection sensor 29 of this fourth embodiment, as shown in FIGS. 8 and 9, the coating body 7, to which the urine introduction ports 8 and the faeces introduction ports 9 are formed, is formed as a lamination body of printed ink layers. More specifically, the lamination body of the coating body 7 includes three printing ink layers 7*a*, 7*b* and 7*c* such that a first solvent resist ink layer 7*a* is printed on the conductors 1, 2, 3 and 4 and the high resistance conductor 14 of the circuit portion which have already been printed, an urine resist ink layer 7*b* is printed on the first layer 7*a*, and a second solvent resist ink layer 7*c* is printed further on the second layer 7*b*. In the printing operations of the respective layers 7*a*, 7*b* and 7*c*, the urine introduction ports 8 and the faeces introduction ports 9 are simultaneously formed.

Polyester resin ink will be used as the solvent resist ink, and as the urine resist ink, there will be used urethane combined ink of polyester polyal and isocyanate, or UV hardened resin ink.

In the case of application of such excrement detection sensor 29 to the diaper, since the conductors 1, 2, 3 and 4 and the high resistance conductor 14 3 are protected by the coating body 7 consisting of the multi-layer structure of the printing ink layers 7*a* to 7*c*, the intrusion of the urine from the urine resist ink layer 7*b* into the conductors 1, 2, 3 and 4 and the high resistance conductor 14 can be prevented. Accordingly, the conductors 1 to 4 and the high resistance conductor 14 at the circuit portion can be also prevented from changing in the resistance values thereof. As a result, urination can be properly detected at a plurality of times, and the excrement receiver 17 and the diaper can be used for the plural urinations. The invasion of the solvent component of the urine resist ink layer 7*b* into the circuit portion can be shut off by the first solvent resist ink layer 7*a*, and the invasion on the side opposite to the circuit portion can be also shut off by the second solvent resist ink layer 7*c*.

Further, in this fourth embodiment of FIGS. 8 and 9, the same reference numerals are added to members or elements corresponding to those in the first to third embodiments and duplicated explanation is omitted herein.

Fifth Embodiment

In the excrement detection sensor of the fifth embodiment, the respective conductors 1 to 4 and 14 in the first to fourth embodiments are printed with a conductive ink including only conductive carbon as conductive substance. Accordingly, the conductors 1 to 4 and 14 exhibit high resistance against urine component, and hence, the variation of the resistance value can be suppressed. As a result, in the case when such excrement detection sensor is applied to the diaper, the urination can be properly detected in plural times.

It is to be noted that the present invention is not limited to the described embodiments and many other changes and modifications may be made without departing from the scopes of the appended claims. For example, although the urine introduction ports and the faeces introduction ports in the first to fifth embodiments are provided for the coating body, these ports may be formed to the carrier body instead of the coating body. In addition, the coating body is formed with the printing ink layers, but it may be formed with a film member as like as the carrier body.

The invention claimed is:

1. An excrement detection sensor comprising: two pairs of conductors extending coaxially in parallel with each other; a carrier body on which the conductors are formed; and
 a coating body covering the conductors with the conductors being disposed between the carrier body and the coating body,
 wherein either one of the carrier body and the coating body is formed with urine introduction ports correlating at least one pair of conductors and faeces introduction ports displaced from the urine introduction ports and correlating another one pair of conductors, in which a plurality of urine introduction ports are disposed in a longitudinal direction of the paired conductors and in which when urine enters into the urine introduction ports, the one pair of the conductors are short-circuited and when faeces enters into the faeces introduction ports, the another one pair of conductors are short-circuited;
 wherein either the one or the another pair of conductors are connected in parallel through a high resistance conductors having a resistance larger than that of the paired conductors.

2. The excrement detection sensor according to claim 1, wherein the conductors are printed on the carrier body, and the coating body is printed so as to cover the printed conductors.

3. The excrement detection sensor according to claim 1, wherein a urine passing hole is formed so as to penetrate the carrier body and the coating body.

4. The excrement detection sensor according to claim 1, wherein the conductors are printed with conductive ink including conductive carbon.

5. The excrement detection sensor according to claim 4, wherein either one or another pair of conductors are connected through a high resistance conductor having a resistance larger than that of the paired conductors and the conductors are printed with conductive ink including conductive carbon of an amount larger than that included in the conductive ink of the high resistance conductor.

6. The excrement detection sensor according to claim 1, wherein the carrier body or coating body formed with the urine introduction ports is formed as a lamination body composed of printing ink layers including at least one layer formed of urine resist ink.

7. The excrement detection sensor according to claim 6, wherein the lamination body includes at least one layer of solvent resist ink disposed between the urine resist ink layer and the conductors.

8. The excrement detection sensor according to claim 6, wherein the urine resist ink is an urethane combined ink of polyester polyal and isocyanate or a UV hardened resin ink.

9. The excrement detection sensor according to claim 7, wherein the solvent resist ink is polyester resin ink.

10. The excrement detection sensor according to claim 1, wherein the conductors are printed with conductive ink including only of conductive carbon as conductive material.

11. The excrement detection sensor according to claim 1, wherein the conductors are printed on the carrier body, and the coating body is printed so as to cover the printed conductors.

12. The excrement detection sensor according to 1, wherein the conductors are printed with conductive ink including conductive carbon.

13. The excrement detection sensor according to claim 12, wherein the conductors are printed with conductive ink including conductive carbon of an amount larger than that included in the conductive ink of the high resistance conductor.

14. The excrement detection sensor according to 1, wherein the conductors are printed with conductive ink including only of conductive carbon as conductive material.

* * * * *